US008544349B2

(12) United States Patent
Zumbrum (10) Patent No.: US 8,544,349 B2
(45) Date of Patent: Oct. 1, 2013

(54) FLUID TRANSFER DEVICE (75) Inventor: Michael A. Zumbrum, New Oxford, PA (US)

(73) Assignee: Allpure Technologies, Inc., New Oxford, PA (US)

( * ) Notice: Subject to any disclaimer, the term of this patent is extended or adjusted under 35 U.S.C. 154(b) by 816 days.

(21) Appl. No.: 12/688,648

(22) Filed: Jan. 15, 2010

(65) Prior Publication Data
US 2010/0123094 A1 May 20, 2010

Related U.S. Application Data (63) Continuation-in-part of application No. PCT/US2008/070482, filed on Jul. 18, 2008.

(51) Int. Cl.
*G01N 1/20* (2006.01)
(52) U.S. Cl.
USPC .......... 73/863.86; 137/625.18; 137/881
(58) Field of Classification Search
USPC .......... 73/863.33, 863.86; 137/625.18, 137/861, 877–878, 881; 251/337; 422/537–538
See application file for complete search history.

(56) References Cited

U.S. PATENT DOCUMENTS

| | | | |
|---|---|---|---|
| 2,685,412 A * | 8/1954 | Schell | 236/68 B |
| 2,767,587 A | 10/1956 | Perkins | |
| 2,859,932 A | 11/1958 | Mackal | |
| 2,872,817 A | 2/1959 | Pitts | |
| 2,994,224 A | 8/1961 | Brown | |
| 3,276,447 A | 10/1966 | Hamilton et al. | |
| 3,736,099 A | 5/1973 | Begg et al. | |
| 3,776,042 A | 12/1973 | Werra et al. | |

(Continued)

FOREIGN PATENT DOCUMENTS

| | | |
|---|---|---|
| DE | 2 161 702 A1 | 6/1973 |
| DE | 3 633 431 A1 | 4/1988 |

(Continued)

OTHER PUBLICATIONS

International Preliminary Report on Patentability for PCT/US2011/021341 (PCT app published as WO-2011/088350 A2), report issued Jul. 2012.*

(Continued)

*Primary Examiner* — Thomas P Noland
(74) *Attorney, Agent, or Firm* — Womble Carlyle Sandridge & Rice LLP; Jacob S. Wharton (57) ABSTRACT

A fluid transfer device for transferring fluid into or out of a fluid vessel, such as a tank, and is particularly useful in transferring fluids with particulates or high viscosity in a substantially aseptic, hygienic, or sterile manner. The device has a body with an elongate passage extending through the body. The body has a proximal end and a distal end. A longitudinally displaceable shaft is disposed in and extends along the passage in the body. A plug sealing the passage is at a first location. A diaphragm sealing the passage is at a second location intermediate the plug and the distal end of the passage. The shaft extends through and is secured to the diaphragm. A fluid transfer opening is located in the passage between the diaphragm and the plug. Longitudinal displacement of the shaft causes the fluid transfer opening to be in fluid communication with a fluid vessel, the diaphragm stretching to accommodate the displacement of the shaft while maintaining an aseptic seal of the passage.

19 Claims, 4 Drawing Sheets

(56) References Cited

U.S. PATENT DOCUMENTS

| | | | |
|---|---|---|---|
| 3,779,082 A | 12/1973 | Galloway | |
| 3,858,449 A | 1/1975 | Singer | |
| 4,018,059 A | 4/1977 | Hatch | |
| 4,244,224 A | 1/1981 | Conn | |
| 4,296,759 A | 10/1981 | Joslin et al. | |
| 4,479,393 A | 10/1984 | Shores | |
| 4,525,127 A | 6/1985 | Welker | |
| 4,527,436 A | 7/1985 | Jones | |
| 4,537,593 A | 8/1985 | Alchas | |
| 4,541,457 A | 9/1985 | Blenkush et al. | |
| 4,557,151 A | 12/1985 | Welker | |
| 4,569,236 A | 2/1986 | Kitchen et al. | |
| 4,587,856 A | 5/1986 | Otis | |
| 4,622,457 A | 11/1986 | Bradley et al. | |
| 4,669,321 A | 6/1987 | Meyer | |
| 4,848,725 A | 7/1989 | Tibbals, Jr. | |
| 4,861,239 A | 8/1989 | Simmons et al. | |
| 4,941,517 A | 7/1990 | Galloway | |
| 5,158,558 A | 10/1992 | Melker et al. | |
| 5,360,413 A | 11/1994 | Leason et al. | |
| 5,463,908 A | 11/1995 | Rosolia | |
| 5,474,546 A | 12/1995 | Ambrisco et al. | |
| 5,535,635 A | 7/1996 | Shaw | |
| 5,868,433 A | 2/1999 | Matkovich et al. | |
| 6,032,543 A | 3/2000 | Arthun et al. | |
| 6,145,810 A | 11/2000 | Connolly et al. | |
| 6,221,041 B1 | 4/2001 | Russo | |
| 6,234,122 B1 | 5/2001 | Kirschbaum et al. | |
| 6,516,677 B1 | 2/2003 | Suter | |
| 6,558,365 B2 | 5/2003 | Zinger et al. | |
| 6,699,229 B2 | 3/2004 | Zinger et al. | |
| 6,715,624 B2 | 4/2004 | Brockwell | |
| 6,916,012 B2 | 7/2005 | Newberg et al. | |
| 7,272,981 B2 | 9/2007 | Bigalke | |
| 7,293,475 B2 | 11/2007 | Furey et al. | |
| 7,293,477 B2 | 11/2007 | Furey et al. | |
| 7,350,535 B2 | 4/2008 | Liepold et al. | |
| 7,578,205 B2 | 8/2009 | Belongia et al. | |
| 7,927,316 B2 | 4/2011 | Prouix et al. | |
| 2006/0065868 A1* | 3/2006 | Strong | 251/63.5 |
| 2006/0142730 A1 | 6/2006 | Proulx et al. | |
| 2007/0106264 A1 | 5/2007 | Proulx et al. | |
| 2008/0149877 A1* | 6/2008 | Bessman | 251/331 |
| 2010/0133459 A1* | 6/2010 | Zumbrum | 251/321 |
| 2011/0155258 A1* | 6/2011 | Zumbrum | 137/68.11 |

FOREIGN PATENT DOCUMENTS

| | | |
|---|---|---|
| DE | 3 701 250 A1 | 7/1988 |
| DE | 6 980 7924 T2 | 1/2003 |
| EP | 0 103 396 A2 | 3/1984 |
| EP | 0 858 589 B1 | 8/1998 |
| EP | 1 329 210 A1 | 7/2003 |
| JP | 2001523525 A | 11/2001 |
| SE | 507448 C2 | 6/1998 |
| SU | 649954 A | 2/1979 |
| WO | WO 86/02450 A1 | 4/1986 |
| WO | WO 91/00215 A | 1/1991 |
| WO | WO 97/16715 A1 | 5/1997 |
| WO | WO 99/26580 A1 | 6/1999 |
| WO | WO 03/90843 A1 | 11/2003 |
| WO | WO 2008-042285 A2 | 4/2008 |
| WO | WO 2008-136720 A1 | 11/2008 |
| WO | WO 2010/008395 A1 | 1/2010 |
| WO | WO 2010/008395 A9 | 1/2010 |
| WO | WO 2010/008396 A2 | 1/2010 |
| WO | WO 2011088350 A2 * | 7/2011 |
| WO | WO 2011/088350 A3 * | 11/2011 |

OTHER PUBLICATIONS

Lynx ST Connectors. Datasheet [online], Millipore Corporation, 2008. Retrieved from the Internet: www.millipore.com (4 pages).

Guidelines for Using The Lynx ST Connector. Technical Brief [online], Millipore Corporation, Retrieved from the Internet: www.millipore.com (2 pages), Apr. 2008.

ITT Dualrange Control Valve. Datasheet [online], Pure-Flo. Retrieved from the Internet: www.ittpureflo.com (2 pages), by Jun. 2011.

Sanitary Inline Bleed and Sample Valves. Datasheet [online], Fluid Line Technology. Retrieved from the Internet: www.fluidlinetech.com (1 page), by Jun. 2011.

Colder Products—Quick Couplings & Fittings for Industrial Applications—Industrial Products. Retrieved from the Internet: <URL: http://www.colder.com/Markets/Industrial/IndustrialProducts/tabid/821/Default.aspx?ProductID=23> (1 page), retrieved Feb. 2010.

Risk Free Connection of Sterilized Single-Use Fluid Path Assemblies to Stainless Steel SIP Systems with Lynx ST (Steam-To) Connectors [online], Millipore Corporation, Retrieved from the internet: www.millipore.com (8 pages), May 2008.

Pure-Flo Solutions, Pure-Flo Radial Seated Tank Bottom Diaphragm Valve. Datasheet [online], ITT Industries, 2001. (2 pages).

ITT Sample & Bleed Valves. Datasheet [online], ITT Corporation, 2006. Retrieved from the Internet: www.ittpureflo.com. (4 pages).

Sanitary Inline Bleed and Sample Valves. Datasheet [online], Fluid Line Technology Corporation. Retrieved from the Internet: www.fluidlinetech.com (1 page), by Jun. 2011.

Casella Sales & Marketing Inc., CSMI Sample Valves. Datasheet [online]. Retrieved from the Internet: www.casellasales.com (2 pages), by Jun. 2011.

Colder Products—Quick Couplings & Fittings for Industrial Applications—Industrial Products. Retrieved from the Internet: <URL: http://www.colder.com/Markets/Industrial/IndustrialProducts/tabid/821/Default.aspx?ProductID=22> (1 page), retrieved Feb. 2010.

Greene, R. and R. D'Aquino, "Disposable equipment: A mainstay in bioprocessing," Chemical Engineering Progress, pp. 10-11 (Nov. 1, 2002), vol. 98, Issue 11.

Haughney, H. and H. Aranha, Disposable processing gains you a competitive edge: enhancing manufacturing capacity with disposable filters, connectors, and membrane chromatography, Biopharm International, p. 50 (Oct. 2003), retrieved Feb . 2010.

Haughney, H. and M. Cardona, Taking disposable processing to the next level: a recent innovation extends the cost, labor and safety benefits of disposable processing to critical clarification and pre-filtration steps used in pharmaceutical manufacturing, Biopharm. Trends, pp. 20-22 (Jun. 2004).

Janetschek, R., "Capsule Filters & Disposable Sterile Processing Systems," Pharmaceutical Processing, p. 8 (Jan. 2001), vol. 18, Issue 1.

Tingley, S., "Plastic factory: disposable biopharmaceutical manufacturing takes a giant leap forward; disposable technologies are quickly beginning to change the face of pharmaceutical cleanroom facility design and economics. (Alternative Manufacturing). (part one of two in series) (related article: Identified Causes of Aseptic Processing Failures)," Clean Rooms, pp. 1-4 (Feb. 2003).

Tingley, S., "Plastic Factory, Part II: the final pieces of the disposable puzzle. (Alternative Manufacturing). (sterile transfer process systems)" Clean Rooms, pp. 1-3 (Jun. 2003).

Wendt, D., Disposable processing systems: how suppliers are meeting today's biotech challenges from fluid handling to filtration, Biopharm International, p. 18 (Jul. 2003).

"New quality of data for bioprocessing bags. (Application Area)." Pharmaceutical Processing. Retrieved from the Internet: <URL: http://www.accessmylibrary.com/coms2/summary_0286-25022745_ITM>, pp. 1-2 (Jan. 2002).

"Rapid Aseptic Fluid Transfer System Introduction" Stedim Biosystems. [online]. Retrieved from the Internet: <URL: http: www.stedim.com/p2A_IDC_introduction.php> (2 pages), retrieved Nov. 2007.

Gore's Preliminary Invalidity Contentions to Plaintiff Millipore Corporation *Millipore Corporation v. W.L. Gore & Associates, Inc.*Civil Action No. 09-10765 DPW) (108 pages), civil action filed Oct. 2009.

"Sip-Able Sample Valve," Datasheet [online]. Retrieved from the Internet: www.fluidlinetech.com (1 page), by Jun. 2011.

"Connecting the Sanitary Flange," Datasheet [online], Millipore Corporation, (pp. 1-2), May 2007.

International Preliminary Report on Patentability (Appln. No. PCT/US2008/070482, filed Jul. 18, 2008) mailed Jan. 27, 2011, pp. 1-6.

International Preliminary Report on Patentability (Appln. No. PCT/US2008/070488, filed Jul. 18, 2008) mailed Jan. 27, 2011, pp. 1-6.
File history of U.S. Appl. No. 60/375,747, filed Apr. 26, 2002.
File history of U.S. Appl. No. 60/500,024, filed Sep. 4, 2003.
Written Opinion of the International Searching Authority (Appln. No. PCT/US2008/070482, filed Jul. 18, 2008) mailed Apr. 16, 2009.
DE 3 701 250 A1 (Carstensen, CA) Jul. 28, 1988 (abstract) [online] Thomson Derwent (2003). Retrieved from Delphion Derwent, Accession No. 1988-213571, pp. 1-2.
DE 3 633 431 A1 (Buhler, R) Apr. 14, 1988 (abstract) [online] Thomson Derwent (2003). Retrieved from Delphion Derwent, Accession No. 1988-106251, pp. 1-3.
DE 2161702 A1 (Heil, E.) Jun. 14, 1973 (abstract) [online] Thomson Innovation (2011). Retrieved from Thomson Innovation, pp. 1-2.
DE 69807924 T2 (Russo, A.) Jan. 9, 2003 (abstract) [online] Thomson Innovation (2011). Retrieved from Thomson Innovation, pp. 1-3.
JP 2001523525 A Nov. 27, 2001 (abstract) [online) Thomson Innovation (2011). Retrieved from Thomson Innovation, pp. 1-2.
SU 649954 A (Vinichenko VP) Feb. 28, 1979 (abstract) [online] 2007 Derwent Information Ltd. Accession No. 1979-83821B, 1 page.
SE 507448 C2 (Nils, A.) Jun. 8, 1998 (abstract) [online} Thomson Innovation (2011). Retrieved from Thomson Innovation, pp. 1-2.

* cited by examiner

FLUID TRANSFER DEVICE

REFERENCE TO RELATED APPLICATION

Priority is hereby claimed to the filing date of PCT Application No. PCT/US2008/070482 filed on Jul. 18, 2008.

TECHNICAL FIELD

This disclosure relates generally to fluid transfer devices, and more specifically to a fluid transfer device for transferring fluid in a substantially aseptic manner.

BACKGROUND

In the manufacturing and processing of many different products, it often is necessary to transfer fluid into or out of a closed processing system and do so in a substantially aseptic, hygienic, or sterile manner without breaching the closed nature of the system. In particular, the need to transfer fluid often arises in the manufacturing and processing of pharmaceuticals, biopharmaceuticals, or other biotechnology applications where processes are conducted in large process tanks, including but not limited to, the transfer of media solutions. The need for fluid transfer arises in other applications and industries as well, including but not limited to, the production of food, cosmetics, paint, chemicals, including hazardous chemicals, and the transfer and handling of semiconductor fluids.

Regardless of the industry, during transfers or sampling the fluid in tanks or other vessels must remain substantially free of contaminants. In addition, when making such transfers, it is desirable to keep the environment surrounding a vessel free from contamination by the contents of the vessel or a sample taken therefrom. It is often the case that throughout the manufacturing process there is a need to take multiple samples from the fluid or, in some circumstances, add additional fluid or media to the fluid in a vessel. To accomplish a substantially aseptic, hygienic, or sterile transfer, it is desirable to control the environment through which the fluid flows, for example, the pathway from a tank to a sample container should be substantially aseptic, hygienic, or sterile along the entire pathway. Furthermore, it is desirable that the fluid transfer device be safe for use, reliable, and of low-cost construction.

It is also desirable to transfer fluid using a device which is pre-sterilized and disposable. A pre-sterilized device avoids the need for an operator to prepare the device for use. In addition, a disposable device avoids the time consuming and laborious task of sterilizing sampling equipment. Further, such sterilization can damage the fluid transfer device and render it useless before its first use.

Pre-sterilized sampling devices that allow for substantially aseptic transfers are disclosed in pending PCT Application No. PCT/US2008/070482, owned by the assignee of the present invention, the entire contents of which are hereby incorporated by reference.

In some instances there arises the need to transfer a media solution having a high particulate content, that contains particles, or is of high viscosity. These media solutions may clog a cannula or hypodermic needle found in some fluid transfer devices. Devices that utilize a hypodermic needle or cannula, like that disclosed in PCT Application No. PCT/US2008/070482, may clog if particles or a media solution with a high particulate concentration or viscosity is transferred through the device. Such media solutions necessitate larger openings to accommodate particulates or increased viscosity without clogging the transfer device. One sampling device that is capable of transferring fluids with particulates is disclosed in U.S. Pat. No. 7,293,477. However, that device lacks a substantially aseptic, hygienic or sterile cavity in the fluid transfer device that ensures that the fluid in the vessel from which a sample may be drawn remains substantially free of contaminants while, at the same time, ensuring that the environment surrounding a vessel remains free from contamination by the contents of the sample.

In addition, there arises the need to transfer media solutions containing cells, live cultures, or proteins. Such media solutions require low sheer and other physical forces to avoid damage to the media's content during a transfer. Devices using a cannula or hypodermic needle may cause such damage.

In view of the above, there exists a need for a fluid transfer device that is inexpensive, pre-sterilized, disposable, capable of being used with standard industrial ports commonly found in fluid receptacles, and capable of use in common industrial settings, such as those found in the pharmaceutical, biopharmaceutical, or other high purity industries, where there is often the need to transfer fluids with particles or high particulate concentrations.

SUMMARY

PCT Application No. PCT/US2008/070482 filed on Jul. 18, 2008, to which priority is claimed above, is hereby incorporated fully by reference.

Briefly described, a fluid transfer device is disclosed for transferring fluid into or from a fluid receptacle, such as a tank, in a substantially aseptic manner. As used herein, the term "aseptic" includes aseptic, hygienic, or sterile conditions. In a first preferred and illustrated embodiment, the device is configured to sample a fluid or other media, such as slurry, from a fluid vessel. As used herein, "fluid" includes high particulate fluids, slurries, or any high viscosity fluid, including without limitation soy-based media or media containing anti-foaming agents, such as silica-based agents. It should be understood, however, that fluid transfer device disclosed herein is not limited to taking samples from a process vessel, and may be used for any type of fluid or media transfer into or out of a fluid vessel, especially when there is a need to maintain aseptic conditions both within the fluid pathway and to protect the environment from the transferred fluid. Additionally, the fluid transfer device disclosed herein provides a fluid pathway that minimizes sheer and other forces that may damage cells or proteins in a media solution.

The device comprises a body with an elongate passage extending through the body. The body has a proximal end and a distal end. The proximal end is that end closest to the fluid vessel into or from which fluid is transferred. The distal end is that end furthest away from the fluid vessel into or from which fluid is transferred. A longitudinally displaceable shaft is disposed in and extends along the passage in the body. The shaft has a proximal end and a distal end that corresponds with the proximal and distal ends of the passage. When actuated, the shaft moves longitudinally within the passage and moves between a first and second position. In its first position, the shaft is displaced toward the distal end of the passage. In its second position the shaft is displaced toward the proximal end of the passage.

A plug is attached to the proximal end of the shaft and, when the shaft is at its first position, the plug seals the passage at the proximal opening. A diaphragm seals the passage at a location intermediate the plug and the distal end of the passage. The shaft extends through and is sealingly secured to the diaphragm. A fluid transfer opening or side port is located in the passage between the plug and diaphragm. The fluid transfer opening provides a pathway for fluid transfer when the device is actuated. A conduit is connected to the fluid transfer opening to assist with the transfer of fluid and to which further conduit or flexible tubing may be attached. Longitudinal displacement of the shaft towards its second position moves the plug and opens the passage. The diaphragm attached to the shaft stretches to accommodate the movement of shaft while maintaining its seal about the shaft and thus maintaining a seal of the distal end of the passage. When the shaft moves the plug and the passage opens, a fluid flow path is established through the passage and fluid transfer opening and further through the conduit attached to the fluid transfer opening. The passage between the plug and diaphragm may be substantially aseptic. In addition, the entire pathway that fluid flows from the fluid vessel to a sample container may be substantially aseptic. The plug may be partially disposed inside the proximal end of the passage before displacement of the shaft from its first position.

The device also includes a tank mount that allows the device to be connected to any standard industrial vessel port or, if desired, a customized port. The tank mount is attached to the fluid transfer device and is also substantially aseptic to meet the needs of the end user. The tank mount contains an opening through which the shaft may pass when the shaft is longitudinally displaced in the proximal direction. The tank mount may include a groove located in the tank mount and a seal located in the groove that allows the formation of a seal between a tank mount and a tank. The tank mount may also comprise a threaded stud for mounting the fluid transfer device to a tank.

In a second preferred and illustrated embodiment, the longitudinally displaceable shaft has a first position displaced toward the proximal end of the passage and a second position displaced toward the distal end of the passage. The shaft is axially biased toward the proximal end of the passage in its first position. Longitudinal displacement of the shaft towards its second position moves the plug and opens the passage. The diaphragm attached to the shaft stretches to accommodate the movement of shaft while maintaining its seal about the shaft and thus maintains a seal of the distal end of the passage. When the shaft moves the plug and the passage opens, a fluid flow path is established between the open end of the passage and a fluid transfer opening in the passage and out through conduit attached to the fluid transfer opening. Like with the first preferred and illustrated embodiment, the passage between the plug and diaphragm may be substantially aseptic and the entire pathway that fluid flows to or from the fluid vessel may also be substantially aseptic. Also like with the earlier embodiment, the plug may be partially disposed inside the proximal end of the passage before displacement of the shaft from its first position.

The fluid transfer devices disclosed herein preferably comprises a tab assembly to which the shaft is connected. The tab assembly controls the displacement of the shaft through the passage regardless of whether displacement occurs in the proximal direction, that is, pushing the tab, or in the distal direction, that is, pulling the tab. The tab assembly preferably comprises a tab guide. Longitudinal displacement of the tab assembly displaces the tab guide through a portion of the passage. Preferably, the shaft is axially biased longitudinally (either distally or proximally) to maintain the plug in a position that seals the proximal end of the passage. In this embodiment, a bias may retract the shaft to a first position after displacement.

The device may also comprise a retaining cap at the distal end of the body. The retaining cap may comprise an opening through which the shaft and tab guide pass. The retaining cap engages the distal end of the body and further comprises restraining means allowing the tab guide and the shaft to move through the retaining cap and stop at a predetermined position. The restraining means may comprise an axial channel extending along the tab guide and a detent extending from the opening in the retaining cap. The detent extends from the opening in the retaining cap into the axial channel along the tab guide. The detent limits the longitudinal displacement of the tab guide in the longitudinal direction and thus assists with keeping the tab guide and entire tab assembly from coming out of the retaining cap and away from the body of the device during operation.

A single fluid transfer device is preferably joined together with additional fluid transfer devices as described in herein to form an assembly having a plurality of bodies. Using multiple devices assembled together allows a user to take multiple samples from a single fluid vessel, either simultaneously or, as is more often the case, over the course of a process. Each sample can be taken without exposing the fluid vessel to the environment and without exposing the environment to the transferred fluid. Alternatively, an assembly of devices may be used to make multiple transfers of media or fluid into a fluid vessel.

Also provided is a kit for transferring fluids or media comprising a fluid transfer device as described herein. The fluid transfer device may comprise one or more bodies joined together. The kit may also contain a tank mount, one or more lengths of flexible tubing, and a plurality of sample containers. In a preferred embodiment the kit is rendered substantially aseptic and packaged to maintain a substantially aseptic state before use.

Thus, a unique fluid transfer device with a substantially aseptic fluid pathway is disclosed that possesses distinct attributes and represents distinct improvements over the prior art. These and other aspects, features, and advantages of the fluid transfer device of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

DETAILED DESCRIPTION

Figures 1, 2, 3:
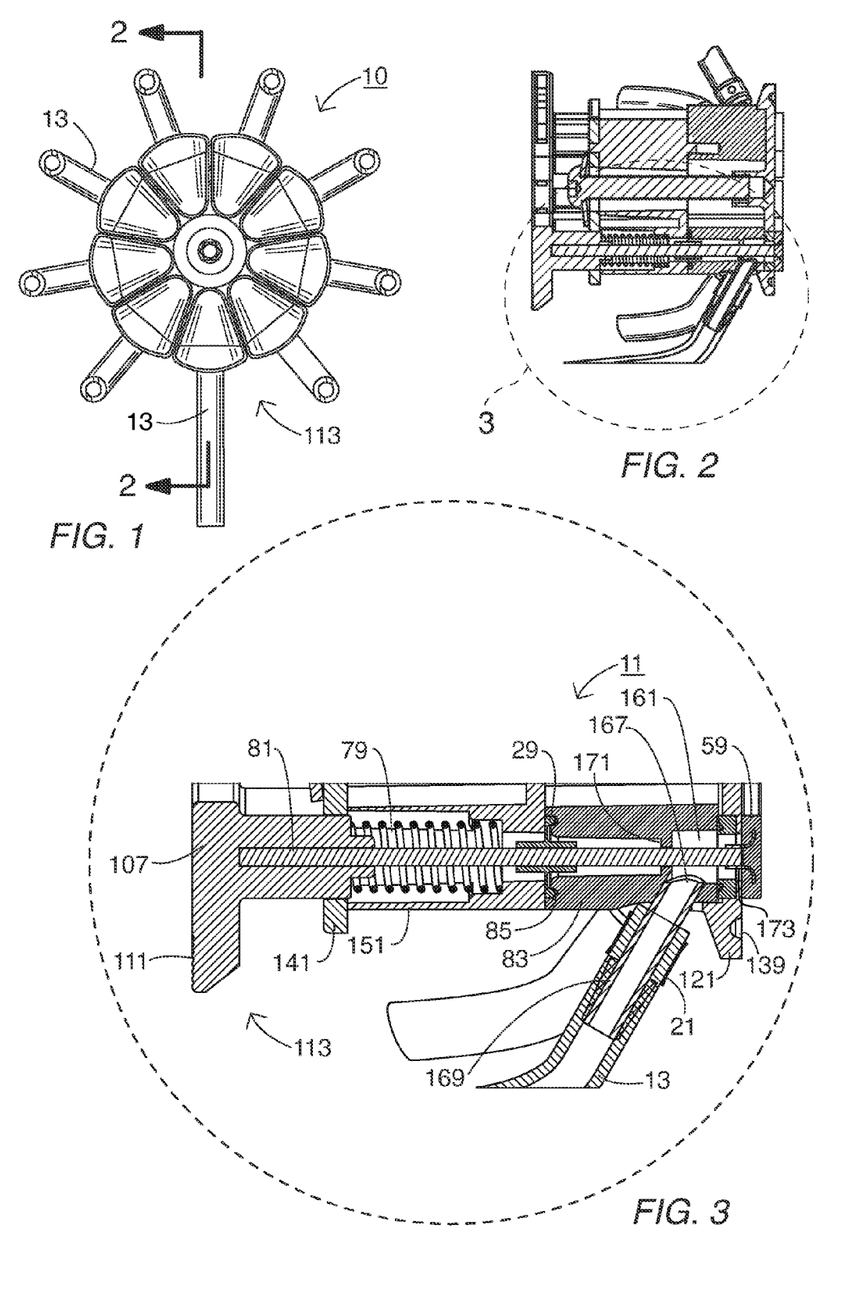
FIG. 1 depicts a fluid sampling device assembly and flexible tubing.
FIG. 2 is a cross-section of a fluid transfer device assembly with the shaft in the first position.
FIG. 3 is a cross section of a fluid transfer device with the shaft in the first position.

Referring now in more detail to the drawing figures, wherein like reference numerals indicate like parts throughout the several views, FIG. 1 depicts a first exemplary fluid sampling device assembly, in this case a device suitable for use with fluids having particulates, such as slurry, a liquid having a high percent solids or a high viscosity liquid, and flexible tubing according to the present disclosure. It should be understood that the fluid transfer device is not limited to use with fluids with particulates or having a high viscosity and may be used with a variety of fluids, including those having no or very little particulate content or low viscosity.

The fluid transfer device illustrated in FIG. 1 depicts nine fluid transfer devices joined together as an assembly of multiple fluid transfer devices that allows for multiple samples to be drawn from a single fluid vessel or, alternatively, for fluid or media to be added to a fluid vessel, such as with inoculations, without opening the fluid vessel to the surrounding environment. The fluid transfer device assembly is not limited to this number of joined fluid transfer devices, but may incorporate more or fewer fluid transfer devices in an assembly. In general, the exemplary fluid transfer device assembly 10 has a circular outer configuration defined by body sections discussed in more detail below. The tab assemblies 113 shown in exemplary fluid transfer device assembly 10 are moved to longitudinally displace shafts from their first position to their second position. As shown in FIG. 1, the shafts are in their first positions.

Figure 4:
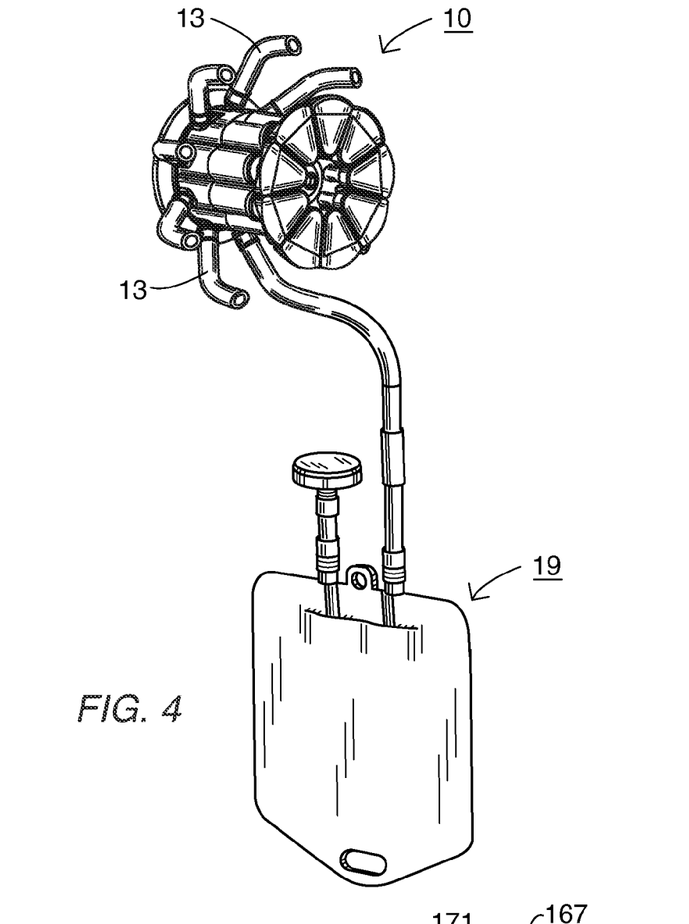
FIG. 4 is a perspective view of a fluid sampling device assembly with flexible tubing and a sample container attached with the shafts in the first position.

In the fluid transfer device assembly illustrated in FIG. 1, flexible tubing 13 is attached to a multiple fluid transfer devices. For clarity, only a portion of the flexible tubing attached to each is shown. In use, flexible tubing may be attached to any number of fluid transfer devices of the assembly depending on the number of transfers needed. Each piece of flexible tubing 13 may be directed away from the fluid transfer device assembly and to a fluid sample container 19 as shown in FIG. 4 and described in greater detail below. The device may be used, for example, to take multiple fluid samples from a fluid vessel, such as a tank, wherein a process is running. The samples may be taken simultaneously or over differing time intervals. The fluid transfer device assembly 10 may be connected to a fluid vessel, such as a tank, prior to a process being performed in the tank. The flexible tubing 13 may be connected to the fluid transfer device assembly 10 prior to connecting to the fluid transfer device 11 to the tank. Likewise, the sample containers 19 may be connected to the flexible tubing 13 prior to connecting the flexible tubing 13 to the fluid transfer device assembly 10 and before the fluid transfer device assembly 10 is connected to a fluid vessel. However, it is understood that the fluid transfer device assembly 10, the flexible tubing 13, and the sample containers 19 may be attached in any order necessary to use the device to transfer fluid. Sample fluid containers suitable for use with the fluid transfer device include without limitation, bags, bottles, syringes, other tanks, tubing, manifolds, vials, or any combination thereof. If desired, more rigid tubing or conduit may be used in place of flexible tubing 13 in which case venting may be necessary.

The flexible tubing 13 may be connected to the fluid transfer device assembly 10 by a crimped collar 21 that affixes the tubing to the distal end of the shaft. However, the flexible tubing 13 may be connected by other means, such as by press-fit, an adhesive, or the like. Likewise, the flexible tubing 13 can be connected to the sample container in similar means.

FIG. 2 shows a cross-section of the fluid transfer device assembly 10. FIG. 3 shows a detailed cross-section of an exemplary fluid transfer device found in the assembly shown in FIGS. 1 and 2. The fluid transfer device 11 comprises an elongate passage therethrough, flexible tubing 13, a crimped collar 21, a plug 59, a spring 79, a longitudinally displaceable shaft 81, a lower portion of a body 83, a diaphragm seat 85, a tab assembly 113, ridges 111 on a tab 107, a tank mount 121, a groove in the tank mount 139, a retaining cap 141, an upper portion of a body 151, a substantially aseptic chamber 161, a fluid transfer opening 167, a fluid transfer conduit 169, a shaft alignment aperture 171, and plug supports 173. With respect to the fluid transfer device 11 and the components therein, there is a proximal end and a distal end. The proximal end is that end closest to the fluid vessel into or from which fluid is transferred. In FIG. 3, the proximal end of the device is the end of the device where the plug 59 is found. The distal end of the device is that end furthest away from the fluid vessel into or from which fluid is transferred and in FIG. 3, the distal end is the end where tab 107 is found. As used throughout this disclosure, the terms "proximal" and "distal" refer to these ends of the fluid transfer devices disclosed herein. However, it should be understood that if a component is located in a proximal or distal direction, it does not need to be at the complete proximal or distal or end of the device. Rather, the component may merely be located in that general direction from the point of reference. Thus the terms "proximal" and "distal" are relative and should be understood to merely aid reference in this disclosure. Similarly, it should be understood that reference to transferring fluid from a vessel is but one intended use of the device and the device may be and is intended to be used to transfer fluid or media into a fluid vessel.

With continued reference to FIG. 3, the longitudinally displaceable shaft 81 (referred to herein occasionally as just "shaft") has a proximal and distal end that corresponds with the proximal and distal ends of the passage. In operation, the shaft travels between a first position and a second position. As shown in FIG. 3, the shaft is in its first position. The shaft extends through and is sealingly attached to a diaphragm 29. The shaft is attached to tab assembly 113 on the distal end of the device. A plug 59 is attached to the proximal end of the shaft. The plug 59 is secured to the shaft using supports 173. The plug may be constructed from silicone or, preferably, from platinum-cured silicone. The plug may also be constructed from a solvent resistant fluoroelastomer, such as a perfluoropolyether elastomer. However, it is understood that plug 59 may be constructed of any suitable material. In FIG. 3, the plug 59 is located outside the proximal end of the passage prior to displacement of the shaft from its first position. However, the plug 59 may also be located at least partially within the inside the passage prior to displacement of the shaft from its first position. The plug may be shaped and located to effectively seal the proximal end of the passage when the shaft is in its first position.

Fluid transfer opening 167 is located in the passage between the proximal opening of the passage and the diaphragm 29 and provides a pathway for fluids to travel upon actuation of the device. A fluid transfer conduit 169 is sealingly attached to the fluid transfer opening and provides a further pathway for fluid to travel. The combination of the fluid transfer opening 167 and fluid transfer conduit 169 allows for fluid to move into the fluid transfer opening 167 and to the flexible tubing 13 and then on to sample containers 19 (not shown in FIG. 3). Alternatively, when fluid or media is transferred into a fluid vessel, the fluid pathway is essentially reversed. Flexible tubing 13 may be securely attached to the fluid transfer conduit 169 using, for example, a crimped collar 21. The space along the passage between the plug 59 and diaphragm 29 creates a chamber 161. This chamber remains substantially aseptic throughout operation and acts to keep the fluid transfer within a closed system from the point the sampled fluid leaves the fluid vessel to its arrival in a sample container.

With continued reference to FIG. 3, the shaft is disposed within a body that is constructed from an upper body portion 151 and a lower body portion 83 that, when joined together, form a unitary body. It should be understood that the body may be formed as a single structure or from two or more portions. The purpose of the body is to enclose and create a passageway in which the components of the fluid transfer device are located and thus the construction of the body may vary to accommodate the number of fluid transfer devices joined in an assembly. As shown, the body has a substantially cylindrical outer portion. Such shape provides for a compact organization of fluid transfer devices, is easily handled, and is similar in shape to the tank mount. Preferably, the body is constructed from high temperature glass reinforced polyester. Alternatively, the body may be constructed of polyvinylidene fluoride, polycarbonate (which provides high temperature resistance), polyether ether ketone (PEEK), or Ultem® (polyetherimide). However, it should be understood that the body may be constructed of any suitable material and its construction is not limited to the materials listed herein. Preferably the body, and in particular the lower body portion 83, contains an alignment aperture 171 that guides the shaft while moving between its first and second positions.

Also depicted in FIG. 3 is tank mount 121. The fluid sample device 11 or fluid sample device assembly 10, as shown in FIG. 1, is joined to a tank mount that allows the fluid sample device or assembly to be joined to any number of fluid vessels that are used in industrial settings. The tank mount is preferably constructed of 316L stainless steel. However, it should be understood that the tank mount may be constructed of any suitable material. The tank mount may also include a groove 139 in which a seal is located to assist with a substantially aseptic connection of the fluid transfer device to a fluid vessel.

In operation the shaft 81 moves between two positions. In its first position, the shaft is displaced toward the distal end of the passage, as shown in FIG. 3. The shaft 81 may be biased in a first position that displaces the shaft toward the distal end of the passage. In other words, the shaft 81 is forced in the distal direction and the plug 59 seals the proximal end of the passage. The bias on the shaft 81 may be created by, for example, the placement of a spring 79, such as shown in FIG. 3. While the shaft is in this first position the plug 59 seals the passage through the body of the device at its proximal end. The diaphragm 29 seals the passage at a location distal from the plug 59 and thus creates the substantially aseptic chamber 161.

Figure 5:
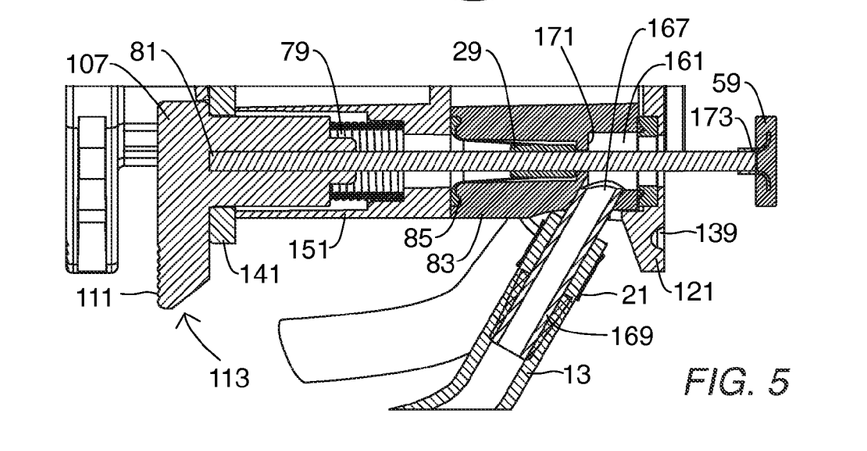
FIG. 5 is a cross-section of a fluid transfer device with the shaft in the second position.

In its second position, as shown in FIG. 5, the shaft is displaced in a proximal direction toward the proximal end of the passage, for example, by a user depressing the tab and pushing the shaft proximally into a fluid vessel. Once displaced, the plug 59 no longer seals the passage and a fluid pathway is created through the proximal end of the passage, into the chamber 161, through the fluid transfer opening 167 and out the fluid transfer conduit 169. The fluid then travels through the flexible tubing 13 and into a fluid sample container. The shaft is maintained in this second position until a sufficient sample of fluid is collected. Alternatively, fluid or media may be added to a fluid vessel by forcing the fluid or media to be added along this fluid pathway and into the fluid vessel.

Figure 6:
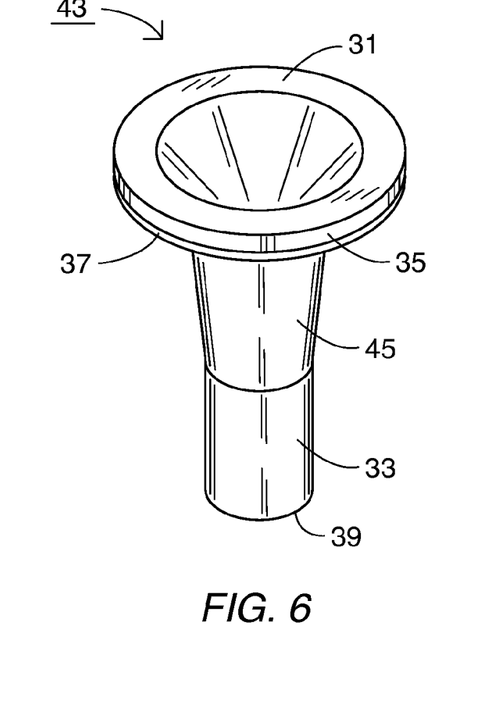
FIG. 6 is a perspective view of an embodiment of a stretched diaphragm.

When the shaft is in its second position the diaphragm 29 stretches while maintaining a seal around the shaft. FIG. 6 illustrates the diaphragm as it appears when stretched along its axis. The stretched diaphragm 43 is made of flexible material and is capable of stretching in at least the direction of its axis. In this illustration, the stretched diaphragm 43 has a top face 31, a central body 33, a side 35, an annular bead 37, and a central opening 39. The central opening 39 is substantially cylindrical to receive the shaft 81. The body receives the annular bead 37 in a seat 85 as shown in FIG. 3. As used in the fluid transfer device disclosed herein, a shaft (see FIGS. 3, 5, 9 and 10) extends through the central opening 39 and is secured to the diaphragm 29 by molding, for example, the diaphragm 29 around the shaft when the diaphragm is produced. However, the diaphragm 29 may be secured to a shaft through other means such as with adhesives or sealants. It is further understood that the central opening 39 may have various shapes.

Figure 7:
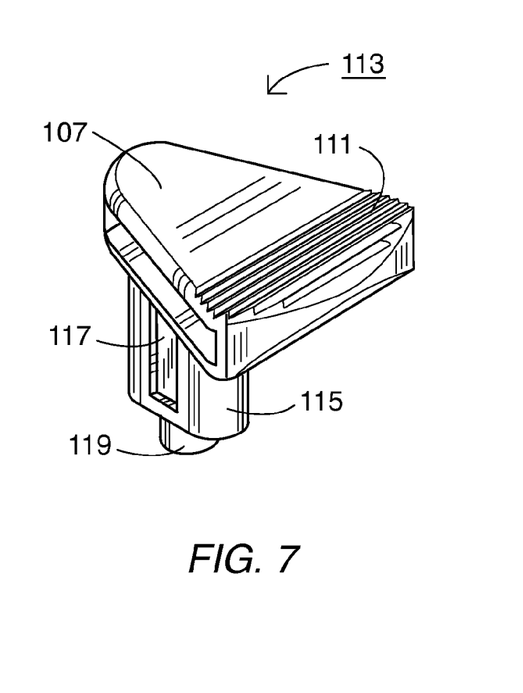
FIG. 7 is a perspective view of an embodiment of a tab assembly.

As shown in FIG. 7, a tab assembly 113 comprises a tab 107, ridges 111 to facilitate operation, a tab guide 115 to guide the tab during use, and an axial channel 117 in the tab guide 115. The shaft 81 may be connected to the tab at the opening 119. Furthermore, a spring, such as that depicted in FIG. 3, may be fitted around the extension in which opening 119 is located. Such arrangement is depicted in detail in FIG. 3.

Figure 8:
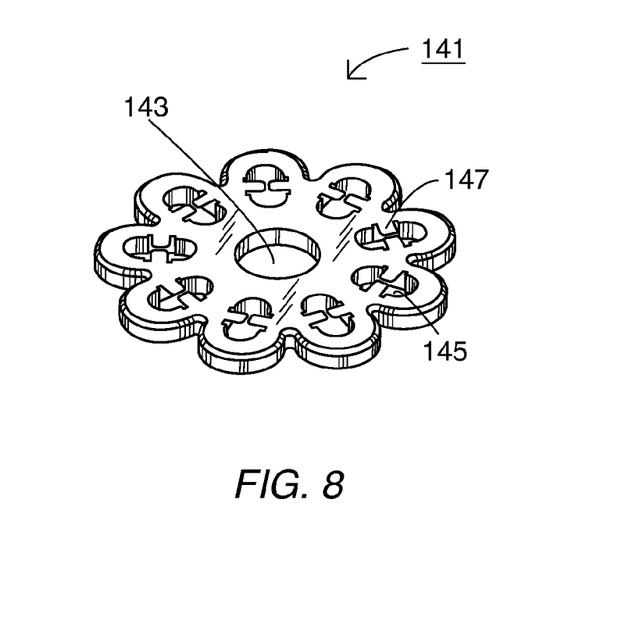
FIG. 8 is a perspective view of an embodiment of a retaining cap.

FIG. 8 illustrates a retaining cap 141, a central opening 143, and openings 145 through which tab guides, such as those depicted in FIG. 7, pass, and detents 147. In an assembled fluid transfer device, the retaining cap 141 is located at the distal end of the upper portion of the body as shown in FIG. 3. The retaining cap 141 may be constructed of a flexible material, such as polycarbonate or polyolefin. Preferably, the retaining cap is constructed of polycarbonate. However, the retaining cap may be constructed from any suitable material. The detents 147 travel in the axial channel 117 of the tab guide 115. Further, the bottom surface of tab 107, that is, the side opposite the ridges 111, contacts the top of the retaining cap 141, thereby limiting the axial travel of tab assembly 113. After a sample is taken, and when the tab 107 is retracted in a distal direction, the extended detents 147 keep the tab assembly 113 from coming out of the retaining cap 141 and potentially tearing the diaphragm and breaking the substantially aseptic state of the fluid transfer device and, in particular, the substantially aseptic chamber 161.

Figure 9:
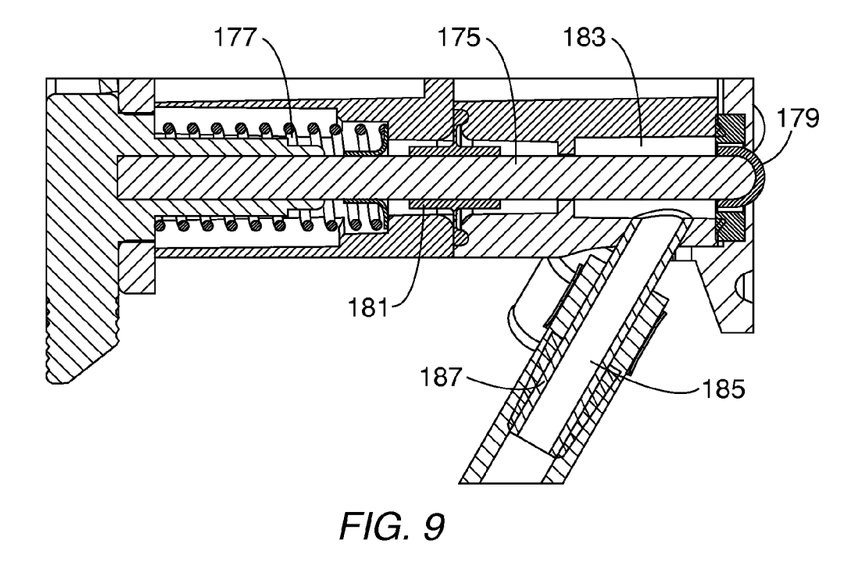
FIG. 9 is a cross-section of a fluid transfer device with the shaft in the first position.

In a second preferred and illustrated embodiment of a fluid transfer device, and as disclosed in FIG. 9, a longitudinally displaceable shaft 175 is disposed in and extends along a passage extending through the body of a fluid transfer device. The shaft 175 moves between two positions wherein in its first position the shaft is displaced toward the proximal end of the passage. The shaft 175 may be biased in a first position that displaces the shaft toward the proximal end of the passage. The bias may be created, for example, by the placement of a spring 177, such as shown in FIG. 9. While the shaft is in this first position a plug 179 seals the passage through the body of the device at its proximal end. Plug 179 is attached to the proximal end of the shaft 175. A diaphragm 181 seals the passage at a location distal from the plug. The portion of the passage between the plug 179 and diaphragm 181 is a chamber 183 that is substantially aseptic. A fluid transfer opening 185 is located in the passage between the proximal opening of the passage and the diaphragm 29 and provides a pathway for fluids to travel upon actuation of the device. A fluid transfer conduit 187 is sealingly attached to the fluid transfer opening 185 and provides a further pathway for fluid to travel. The combination of the fluid transfer opening 185 and the fluid transfer conduit 187 allows for fluid to move into or out of the fluid transfer opening 185 and to the flexible tubing, which may be secured to the fluid transfer conduit 187 as described above.

Figure 10:
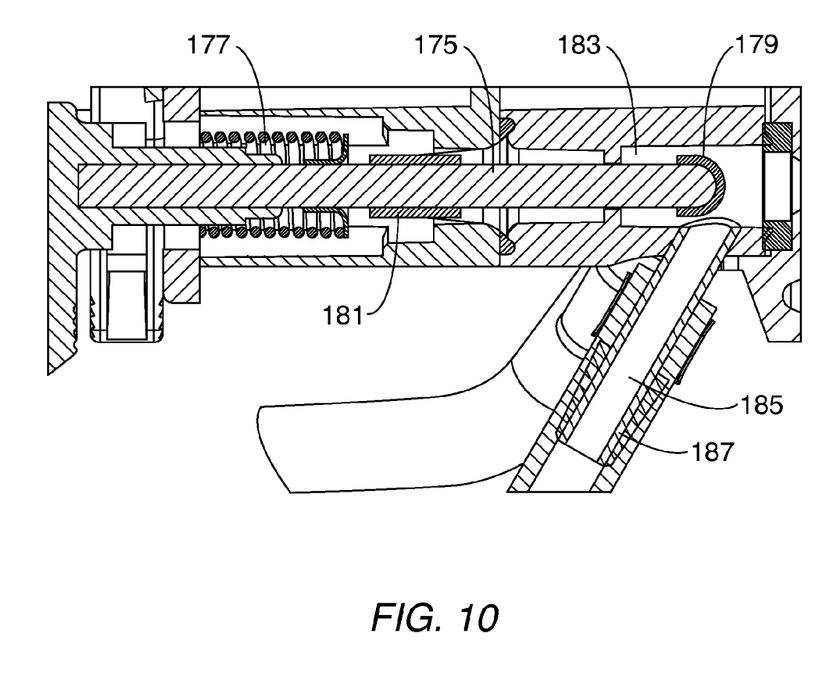
FIG. 10 is a cross-section of a fluid transfer device with the shaft in the second position.

In its second position, as shown in FIG. 10, the shaft is displaced toward the distal end of the passage, for example, by the user pulling the tab and thus pulling the shaft 175 and plug 179 distally away from a fluid vessel. Once displaced, the shaft 175 and plug 179 no longer create a seal at the proximal end of the passage and fluid now enters the passage up to the location of the diaphragm 181 which maintains a seal around the distally displaced shaft. A fluid flow path is now created between the open end of the passage and the fluid transfer opening 185 and through the fluid transfer conduit 187. The fluid then travels through the flexible tubing and into a fluid sample container. The shaft is left in this second position until a sufficient sample of fluid is collected. Alternatively, the device in this embodiment may be used to transfer fluid or media into a fluid vessel as discussed in greater detail above. When the shaft is in its second position the diaphragm 181 stretches while maintaining a seal around the shaft. FIG. 6 illustrates the diaphragm as it appears when stretched along its axis.

The fluid transfer devices disclosed herein may be sold pre-sterilized. Preferably, the entire passageway that fluid will travel is substantially aseptic until use. For example, and referring to FIG. 3, the tank mount 121, plug 59, shaft 81, passage 161, diaphragm 29, and flexible tubing 13 are all substantially aseptic. By rendering and maintaining the pathway that fluid travels substantially aseptic, the fluid may be transferred from one vessel to another without risk of contamination to the fluid. Further, the unique aspect of chamber 161 prevents the contamination of the environment around the fluid transfer device and maintains a completely closed fluid pathway before, during, and after actuation of the device.

Also provided is a kit containing a fluid transfer device assembly 10 as described herein, that is, comprising one or more bodies joined together, one or more lengths of flexible tubing 13 as described herein, a plurality of sample containers 19 as described herein, and a tank mount 121 as described herein.

The fluid transfer device assembly 10 may be assembled and then the entire device or components thereof may be rendered substantially aseptic by, for example, gamma radiation. Alternatively, the entire device or components thereof may be rendered substantially aseptic by exposure to steam above 121° C. for a period of time long enough to eliminate microorganisms. The entire device or components thereof may also be rendered aseptic by chemical treatment, such as with ethylene oxide (ETO). Once rendered substantially aseptic, the device may be appropriately packaged and stored to maintain the substantially aseptic state until ready for use.

A further advantage to the fluid transfer device disclosed herein is the absence of pumps or other mechanical means to transfer fluids. The device disclosed herein transfers fluid using gravity and the existing pressure inside a fluid vessel. The absence of pumps or other mechanical means fewer surfaces to render substantially aseptic and that particulates in the fluid are not damaged by the forces often exerted by mechanical pumps.

All dimensional information presented herein and included in the drawings is intended to be illustrative and not intended to limit the scope of the invention.

The foregoing descriptions of fluid transfer devices illustrate and describe various embodiments considered to represent best modes of carrying out the invention. As various changes can be made in the above embodiments without departing from the scope of the fluid transfer device disclosed and claimed herein, it is intended that all matter contained in the above description or shown in the accompanying drawings shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

What is claimed is:

1. A fluid transfer device comprising:
   a body;
   an elongate passage extending through the body and having a proximal end and a distal end;
   a longitudinally displaceable shaft disposed in and extending along the passage, the shaft having a proximal end and distal end and having a first position displaced toward the distal end of the passage and a second position displaced toward the proximal end of the passage; wherein the shaft is axially biased longitudinally away from the proximal end of the passage;
   a plug attached to the proximal end of the shaft and sealing the passage at the proximal end thereof when the shaft is in its first position;
   a diaphragm sealing the passage at a location intermediate the plug and the distal end of the passage;
   the shaft extending through and being sealingly secured to the diaphragm;
   a fluid transfer opening in the passage between the plug and the diaphragm;
   wherein longitudinal displacement of the shaft towards its second position moves the plug to open the passage, the diaphragm stretches to accommodate the displacement of and maintain a seal about the shaft, and a substantially aseptic fluid flow path is established between the open end of the passage and the fluid transfer opening.

2. The device of claim 1, further comprising a substantially aseptic tank mount.

3. The device of claim 2, wherein the tank mount defines an opening, the shaft passing through the opening when displaced to its second position.

4. The device of claim 1, wherein the plug is disposed outside the proximal end of the passage prior to displacement of the shaft from its first position.

5. The device of claim 1, wherein the plug is disposed at least partially inside the proximal end of the passage prior to displacement of the shaft from its first position.

6. The device of claim 1, wherein the diaphragm is constructed of a silicone elastomer.

7. The device of claim 1, wherein the diaphragm is constructed of a solvent resistant fluoroelastomer.

8. The device of claim 1, wherein the plug is constructed of a silicone elastomer.

9. The device of claim 1, wherein the plug is constructed of a solvent resistant fluoroelastomer.

10. The device of claim 1, further comprising a tab assembly to which the shaft is connected, the tab assembly controlling the displacement of the shaft through the passage.

11. The device of claim 10, wherein the tab assembly further comprises a tab guide, wherein longitudinal displacement of the tab assembly displaces the tab guide through a portion of the passage.

12. The device of claim 11, further comprising a retaining cap at a distal end of the body through which the shaft and tab guide pass.

13. The device of claim 12, wherein the retaining cap engages a distal end of the body and further comprises restraining means to allow the tab guide and the shaft to move through the retaining cap and stop at a predetermined position.

14. The device of claim 13, wherein the restraining means comprises an axial channel extending along the tab guide and a detent extending from the opening in the retaining cap into the axial channel, whereby the detent limits longitudinal displacement of the tab guide so as to limit a range of movement of the tab guide.

15. The device of claim 1, wherein the shaft is axially biased longitudinally away from the proximal end of the passage.

16. The device of claim 1, wherein the body comprises a substantially cylindrical outer portion, at least one alignment aperture for the shaft, and a seat for the diaphragm.

17. A fluid transfer device comprising:
a plurality of bodies joined together, each body comprising:
an elongate passage extending through the body and having a proximal end and a distal end;
a longitudinally displaceable shaft disposed in and extending along the passage, the shaft having a proximal end and distal end and having a first position displaced toward the distal end of the passage and a second position displaced toward the proximal end of the passage;
a plug attached to the proximal end of the shaft and sealing the passage at the proximal end thereof when the shaft is in its first position;
a diaphragm sealing the passage at a location intermediate the plug and the distal end of the passage;
the shaft extending through and being sealingly secured to the diaphragm;
a fluid transfer opening in the passage between the plug and the diaphragm;
wherein longitudinal displacement of the shaft towards its second position moves the plug to open the passage, the diaphragm stretches to accommodate the displacement of and maintain a seal about the shaft, and a substantially aseptic fluid flow path is established between the open end of the passage and the fluid transfer opening.

18. A kit for transferring fluid comprising:
a fluid transfer device comprising:
one or more bodies joined together, each body comprising:
an elongate passage extending through the body and having a proximal end and a distal end;
a longitudinally displaceable shaft disposed in and extending along the passage, the shaft having a proximal end and distal end and having a first position displaced toward the distal end of the passage and a second position displaced toward the proximal end of the passage;
a plug attached to the proximal end of the shaft and sealing the passage at the proximal end thereof when the shaft is in its first position;
a diaphragm sealing the passage at a location intermediate the plug and the distal end of the passage;
the shaft extending through and being sealingly secured to the diaphragm;
a fluid transfer opening in the passage between the plug and the diaphragm;
wherein longitudinal displacement of the shaft towards its second position moves the plug to open the passage, the diaphragm stretches to accommodate the displacement of and maintain a seal about the shaft, and a substantially aseptic fluid flow path being established between the open end of the passage and the fluid transfer opening;
a tank mount;
one or more lengths of flexible tubing; and
a plurality of sample containers.

19. The kit of claim 18, wherein the fluid transfer device, tank mount, one or more lengths of flexible tubing, and plurality of sample containers are substantially aseptic.

* * * * *